United States Patent
Derain

(10) Patent No.: US 9,226,989 B2
(45) Date of Patent: Jan. 5, 2016

(54) FILM-FORMING COMPOSITION, AND USE THEREOF FOR TREATING HERPES

(75) Inventor: Nathalie Derain, Prenois (FR)

(73) Assignee: LABORATOIRES URGO, Chenove (FR)

( * ) Notice: Subject to any disclaimer, the term of this patent is extended or adjusted under 35 U.S.C. 154(b) by 190 days.

(21) Appl. No.: 14/127,237

(22) PCT Filed: Jun. 21, 2012

(86) PCT No.: PCT/FR2012/051417
§ 371 (c)(1),
(2), (4) Date: Dec. 18, 2013

(87) PCT Pub. No.: WO2012/175879
PCT Pub. Date: Dec. 27, 2012

(65) Prior Publication Data
US 2014/0130711 A1    May 15, 2014

(30) Foreign Application Priority Data

Jun. 22, 2011   (FR) ...................................... 11 55493

(51) Int. Cl.
| | | |
|---|---|---|
| *A61Q 17/00* | (2006.01) | |
| *A61Q 19/00* | (2006.01) | |
| *A61L 26/00* | (2006.01) | |
| *A61K 9/00* | (2006.01) | |
| *A61K 47/38* | (2006.01) | |
| *A61K 9/70* | (2006.01) | |

(52) U.S. Cl.
CPC ........... *A61L 26/0023* (2013.01); *A61K 9/0014* (2013.01); *A61K 9/7015* (2013.01); *A61K 47/38* (2013.01)

(58) Field of Classification Search
CPC .................................................. A61Q 17/00
See application file for complete search history.

(56) References Cited

U.S. PATENT DOCUMENTS

| | | | | |
|---|---|---|---|---|
| 4,374,126 | A | * | 2/1983 | Cardarelli et al. .......... 514/772.6 |
| 4,783,335 | A | * | 11/1988 | Lipshitz ......................... 424/407 |
| 5,888,494 | A | * | 3/1999 | Farrar et al. ................ 424/78.05 |
| 5,906,814 | A | * | 5/1999 | Epstein ...................... 424/78.02 |
| 5,981,605 | A | * | 11/1999 | Thomsen et al. .............. 514/724 |
| 8,349,368 | B2 | * | 1/2013 | Gordon et al. ................. 424/659 |
| 2007/0099819 | A1 | * | 5/2007 | Glidden ............................. 514/2 |
| 2010/0048598 | A1 | * | 2/2010 | Kandavilli et al. ........... 514/275 |
| 2010/0297043 | A1 | * | 11/2010 | Lowndes et al. ................ 424/59 |

FOREIGN PATENT DOCUMENTS

| | | |
|---|---|---|
| FR | 2783832 | 3/2000 |
| MD | 1779 F1 | 11/2001 |
| WO | 90/01046 | 2/1990 |
| WO | 97/25018 | 7/1997 |
| WO | 99/49835 | 10/1999 |
| WO | 2004/021968 | 3/2004 |
| WO | 2005/070378 | 8/2005 |
| WO | 2007/147052 | 12/2007 |
| WO | 2008/070602 | 6/2008 |

OTHER PUBLICATIONS

International Search Report in PCT/FR2012/051417 dated Jul. 25, 2012.

* cited by examiner

*Primary Examiner* — Melvin C Mayes
*Assistant Examiner* — Colette Nguyen
(74) *Attorney, Agent, or Firm* — McAndrews, Held & Malloy Ltd.; Nabeela Rasheed

(57) ABSTRACT

The present invention relates to a topical film-forming composition including, in a pharmaceutically acceptable medium: 5 to 30 wt % of ethyl cellulose; 0.1 to 10 wt % of an auxiliary film-forming agent; 0.1 to 20 wt % of one or more triacids, at least one of which is boric acid; and 60 to 95 wt % of an organic solvent, the percentages being expressed by weight relative to the total weight of the composition. The invention also relates to the use of such a composition in a method for treating herpes, in particular herpes labialis.

19 Claims, No Drawings

FILM-FORMING COMPOSITION, AND USE THEREOF FOR TREATING HERPES

The present application is filed pursuant to 35 U.S.C. 371 as a U.S. National Phase application of International Patent Application No. PCT/FR2012/051417, which was filed Jun. 21, 2012, claiming the benefit of priority to French Patent Application No. 115493, which was filed on Jun. 22, 2011. The entire text of the aforementioned applications is incorporated herein by reference in its entirety.

The subject of the present invention is an ethylcellulose-based film-forming composition allowing the formation of a protective film on the skin or on the mucous membranes, and also the use thereof in the treatment of skin lesions, in particular of herpes.

The herpes virus (Herpes Simplex Virus or HSV) is present in a large portion of the population. Although most of the time the infection is asymptomatic, it can cause skin lesions in the form of vesicular eruptions, in particular at the mucosal level. These eruptions, which begin with the simple itching and the appearance of redness, lead in a few hours to the development of papules. As they mature, the papules become blisters and then vesicles containing a clear liquid. The vesicles finally burst, thus releasing the liquid. At this stage, the risk of transmission or of propagation of the virus is particularly high. The vesicles then leave behind a wound which forms a scab before healing. The latter stages of development of the eruption prove, in addition, to be particularly painful.

Local herpetic eruptions, commonly called cold sores in the case of herpes labialis, are most commonly treated by applying compositions in the form of an ointment, a salve or a gel comprising active agents. However, because of the movements and/or rubbing which occurs on the treatment areas concerned, these compositions have a tendency not to remain localized on the wound, thus limiting the action of the active agents. The application of these compositions to the area to be treated therefore needs to be frequently repeated.

In addition, this type of galenical formulation does not make it possible to form an effective barrier to the herpes virus, which is however very contagious. Compositions of patch type, which are more occlusive, have thus been proposed for the treatment of herpes labialis, but these patches cause an unpleasant foreign body sensation when they are applied to the areas to be treated.

Other solutions consist of the use of film-forming compositions. Thus, document U.S. Pat. No. 5,081,158 describes a film-forming composition based on hydroxypropylcellulose (HPC) which makes it possible to prolong the maintaining of active agents on the area to be treated.

Document EP-A-679390 describes, for its part, a sprayable topical formulation for treating the skin or mucous membranes, and in particular herpetic lesions, comprising an active agent dispersed in an aqueous solution of cellulose-based polymer. This composition makes it possible in particular to avoid touching the lesions with the fingers during application, which can prove to be very painful.

Document EP-A-289900 discloses that the skin penetration of an antibacterial agent can be improved by administering said agent in a film-forming composition comprising a water-insoluble polymer, a vegetable oil and a volatile solvent.

However, the films formed by the compositions proposed in these documents have the drawback of not forming an effective barrier with respect to propagation of the herpes virus.

There is therefore a need for film-forming compositions intended for the treatment of herpes, in particular of herpes labialis, which form a film impermeable to HSV and to external bacteria, so as to prevent any contamination of the herpes wound to be treated, and any spread of HSV to individuals not carrying the virus.

The applicant company has therefore developed a film-forming composition enabling the formation of a film which forms an effective barrier with respect to the propagation of the herpes virus. Furthermore, the composition according to the invention has the advantage of being impermeable to infectious agents.

The film thus obtained makes it possible both to protect the lesion against intrusion of bacteria, thus preventing the risk of superinfection, and to avoid the propagation of the herpes virus responsible for the lesion to healthy individuals.

Thus, the present invention relates to a topical film-forming composition comprising, in a pharmaceutically acceptable medium:

- 5% to 30% by weight, preferably 8% to 20% by weight, of ethylcellulose;
- 0.1% to 20% by weight, preferably 2% to 12% by weight, of an auxiliary film-forming agent;
- 0.1% to 5% by weight, preferably 0.5% to 2% by weight, of one or more triacids, at least one of which is boric acid; and
- 60% to 95% by weight, preferably 65% to 85% by weight, of an organic solvent, the percentages being expressed by weight relative to the total weight of the composition.

The film obtained with the compositions according to the invention is flexible and comfortable and does not cause, in particular, any discomfort or any foreign body sensation when it applied to the area to be treated.

According to one preferred embodiment, the film obtained with the compositions according to the invention is colorless.

For the purpose of the present application, the term "topical composition" is intended to mean a form of administration of a composition on a predetermined region of the body.

According to the invention, the topical composition may be a solution, a gel, a cream, an ointment, a lotion or a varnish.

The invention also relates to the use of such a composition for the treatment of herpes, in particular herpes labialis.

Ethylcelluose

The composition according to the invention comprises at least one film-forming ethylcellulose polymer. It has in fact been observed that the introduction of ethylcellulose into pharmaceutical or dermatological topical compositions makes it possible to improve the adhesion, the resistance to rubbing, the viscosity and the hydrophobicity of these compositions.

Ethylcellulose is a film-forming polymer.

The term "film-forming polymer" is intended to mean a polymer capable of forming, by itself or in the presence of an auxiliary film-forming agent, a continuous and adherent film on a support, in particular on the skin or the mucous membranes.

Ethylcellulose is an ethyl ether of cellulose and is in the form of a polymer comprising long chains consisting of anhydroglucose units which are linked to one another by acetal groups.

Each anhydroglucose unit has three totally or partially substitutable hydroxyl groups which can react according to the following reaction scheme:

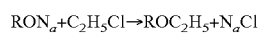

$$RON_a + C_2H_5Cl \rightarrow ROC_2H_5 + N_aCl$$

The substitution of the three hydroxyl groups would confer on each anhydroglucose unit a degree of substitution of 3 or an ethoxyl content of 54.88%.

The ethylcellulose polymers usable in the composition according to the invention are in particular those which have a degree of substitution of their hydroxyl groups of between 2.5 and 2.60 per anhydroglucose unit, or the ethoxyl content of which is between 44% and 50% per anhydroglucose unit.

By way of nonlimiting examples of ethylcellulose polymers that can be used in the context of the present application, mention may be made of those manufactured by Dow Chemical Corporation (Midland, Mich.) and sold under the name "Ethocel", or those which are manufactured by Hercules, Inc (Wilmington, Del.).

The composition according to the invention comprises 5% to 30% by weight, preferably 8% to 20% by weight, and more preferentially 8% to 15% by weight, of ethylcellulose, relative to the total weight of the composition.

Auxiliary Film-Forming Agent

In order to improve the film-forming properties of the composition, an auxiliary film-forming agent can advantageously be added.

The auxiliary film-forming agent is, of course, different than the organic solvent.

Such an auxiliary film-forming agent can be chosen from all the compounds known to those skilled in the art as being capable of performing the desired function. It is in particular chosen from plasticizers and coalescence agents of the film-forming polymer(s).

Thus, the composition may also comprise at least one plasticizer and/or one coalescence agent. In particular, mention may be made, alone or as a mixture, of the usual plasticizers and coalescence agents, such as:
  fatty alcohols, for instance octyldodecanol, 2-butyloctanol, 2-hexyldecanol, 2-undecylpentadecanol or oleyl alcohol;
  glycols and derivatives thereof, such as glycerol, diethylene glycol ethyl ether, diethylene glycol methyl ether, diethylene glycol butyl ether or else diethylene glycol hexyl ether, ethylene glycol ethyl ether, ethylene glycol butyl ether or ethylene glycol hexyl ether;
  fatty acids, such as oleic acid, linoleic acid or linolenic acid;
  glycol esters, such as triacetin (or glyceryl triacetate);
  propylene glycol derivatives, and in particular propylene glycol phenyl ether, propylene glycol diacetate, dipropylene glycol ethyl ether, tripropylene glycol methyl ether and propylene glycol butyl ether;
  acid esters, in particular carboxylic acid esters, such as citrates, phthalates, adipates, carbonates, tartrates, phosphates or sebacates and in particular monocarboxylic acid esters, such as isononyl isononanoate, oleyl erucate or 2-octyldodecyl neopentanoate;
  oxyethylenated derivatives, such as oxyethylenated oils, in particular vegetable oils, such as sesame oil, castor oil, almond oil, canola oil, hazelnut oil, pistachio oil, linseed oil, borage oil, flaxseed oil, jojoba oil, sunflower oil, wheat germ oil, corn and/or corn germ oil, groundnut oil, avocado oil, safflower oil, rapeseed oil, olive oil, argan oil, sunflower oil, grapeseed oil, soybean oil, walnut oil, marrow seed oil, palm oil, coconut oil, and mixtures thereof. The oil may also be a derivative of one of the vegetable oils mentioned above. It may be a hydrogenated or nonhydrogenated, and peroxidized or nonperoxidized oil;
  and mixtures thereof.

According to one preferred embodiment, the auxiliary film-forming agent is chosen from oxyethylenated derivatives, such as oxyethylenated oils, in particular vegetable oils, such as castor oil.

According to a more preferred embodiment, the auxiliary film-forming agent is castor oil.

The auxiliary film-forming agent is present in the composition according to the invention in a content ranging from 0.1% to 20%, and preferably from 2% to 12% by weight, relative to the total weight of the composition.

Triacid

The composition according to the invention also comprises one or more triacids, at least one of which is boric acid.

The triacid makes it possible in particular to improve the cohesion and consequently the mechanical properties of the film.

Advantageously, the triacid is chosen from one or more inorganic or organic triacids, such as phosphoric acid, boric acid or citric acid, or mixtures thereof.

In particular, the composition according to the invention preferably comprises a mixture of boric acid and citric acid, preferably in a weight ratio of between 1:2 and 2:1, preferably 1:1.

The triacid is present in the composition according to the invention in a content ranging from 0.1% to 5% by weight, preferably from 0.5% to 2% by weight, relative to the total weight of the composition.

The combination, in the compositions according to the invention, of an ethylcellulose polymer, an organic solvent and at least one triacid confers particularly unexpected properties on the film obtained, such as, in particular, an excellent impermeability of the film to viruses and to bacteria, and an integrity of the structure of the film throughout the application.

Organic Solvent

The composition according to the invention comprises at least one organic solvent.

The organic solvent may in particular be chosen from:
  ketones, such as methyl ethyl ketone, methyl isobutyl ketone, diisobutyl ketone, isophorone, cyclohexanone or acetone;
  alcohols that are liquid at ambient temperature, such as ethanol, isopropanol, diacetone alcohol, 2-butoxyethanol, cyclohexanol, n-propanol or n-butanol;
  propylene glycol ethers that are liquid at ambient temperature, such as propylene glycol monomethyl ether, propylene glycol monomethyl ether acetate or dipropylene glycol mono-(n-butyl) ether;
  glycols, such as ethylene glycol, propylene glycol, pentylene glycol or glycerol;
  cyclic ethers, such as γ-butyrolactone;
  short-chain esters (having from 3 to 8 carbon atoms in total), such as ethyl acetate, butyl acetate, methyl acetate, propyl acetate, isopropyl acetate, isopentyl acetate, methoxypropyl acetate or butyl lactate;
  ethers, such as diethyl ether, dimethyl ether or dichlorodiethyl ether;
  alkanes that are liquid at ambient temperature, such as decane, heptane, dodecane or cyclohexane,
  alkyl sulfoxides, such as dimethyl sulfoxide;
  aldehydes that are liquid at ambient temperature, such as benzaldehyde or acetaldehyde;
  ethyl 3-ethoxypropionate;
  carbonates, such as propylene carbonate or dimethyl carbonate;
  acetals, such as methylal;
  and mixtures thereof.

According to one preferred embodiment, the organic solvent is volatile.

The term "volatile organic solvent" is intended to mean an organic solvent which is capable of evaporating on contact with the skin in less than one hour, at ambient temperature and atmospheric pressure. The volatile organic solvent is liquid at ambient temperature, has in particular a non-zero vapor pressure at ambient temperature and atmospheric pressure, and in particular it has a vapor pressure ranging from 0.13 Pa to 40 000 Pa ($10^{-3}$ to 300 mmHg), and preferably ranging from 1.3 Pa to 8000 Pa (0.01 to 60 mmHg).

According to one particularly preferred embodiment, the organic solvent is chosen from alcohols which are liquid at ambient temperature, such as ethanol, isopropanol, diacetone alcohol, 2-butoxyethanol, cyclohexanol, and mixtures thereof, and preferably ethanol.

According to a more preferred embodiment, the organic solvent used in the compositions according to the invention is ethanol.

The organic solvent may represent 60% to 95% by weight, preferably 65% to 85% by weight, and preferably 65% to 80% by weight, relative to the total weight of the composition.

Pharmaceutically Acceptable Medium

The composition according to the invention comprises a pharmaceutically acceptable medium which may contain water.

For the purpose of the present application, the term "pharmaceutically acceptable medium" is intended to mean a medium which is compatible with the skin.

The water may in particular be present in the composition according to the invention in a content ranging from 1% to 20% by weight and preferably from 5% to 15% by weight.

In particular, the composition comprises a mixture of water (i.e. as pharmaceutically acceptable medium) and ethanol (i.e. as organic solvent) in a weight ratio of between 1:2 and 1:10, preferably between 1:4 and 1:8 and more preferably between 1:5 and 1:6 by weight.

Additives

The composition according to the invention may comprise one or more pharmaceutically acceptable additives, for instance fragrances, flavorings, dyes, pigments, matting agents, rheological agents, preservatives, depigmenting agents, moisturizing agents, sunscreens and restructuring agents.

Active Agents

In one particular embodiment, the composition according to the present invention does not contain any pharmaceutically active agents.

This is because the inventors have observed, surprisingly, that a film formed by applying a composition according to the invention to an area of skin or of mucous membrane which has a herpetic eruption enables the treatment thereof, even and especially when the composition according to the invention does not contain any pharmaceutically active agent.

Use of the Composition

According to one particular embodiment, the subject of the invention is the composition as previously defined, for use thereof in a method for treating herpes, in particular herpes labialis.

The subject of the invention is also, according to another embodiment, the composition as previously defined, for use thereof in a method for healing wounds caused by the herpes virus, on the skin or the mucous membranes.

By applying the composition according to the invention to a herpetic eruption as soon as the first warning signs of the lesion occur (itching, stinging, redness), it is possible to limit the formation of papules. When it is applied after the formation of the papules, the composition according to the invention contributes to limiting the formation of vesicles and of scabs.

Finally, the film obtained with the compositions of the invention also make it possible to promote healing of the herpetic eruption.

The present invention is illustrated in greater detail in the nonlimiting examples described hereinafter.

EXAMPLES

Example 1

Preparation of Composition A

A composition A according to the invention was prepared in the following way:

| Ingredient | % by weight |
|---|---|
| Ethylcellulose | 10 |
| Castor oil | 10 |
| Boric acid | 0.5 |
| Citric acid | 0.5 |
| Ethanol | 67 |
| Demineralized water | 12 |

The castor oil, the boric acid and the citric acid were added to the water/ethanol mixture with stirring maintained for 10 min. The ethylcellulose was then dispersed in the mixture. Composition A was recovered after stirring the mixture for 30 min.

Example 2

Evaluation of the Impermeability of the Film Obtained With Composition A to Infectious Agents 1. Material:

The cells used are Vero cells originating from the ATCC CCL-81 or from the Medical Virology Laboratory of the Institut Pasteur (Yasumunra Y. et al, 1962). These cells derive from an African green monkey kidney.

The culture and titration medium is a DMEM medium ("Dulbecco/Vogt modified Eagle's Minimal Essential Medium") supplemented with 2% of glutamine, 4% of FCS and 1% of gentamicin sulfate.

The dilution medium is a DMEM medium supplemented with 2% of glutamine or 1% of gentamicin sulfate.

The virus used is the PseudoRabies Virus (PRV) (Aujesky's disease virus): ATCC VR-135 (Aujesky A., 1902; Roiznan R. et al., 1981).

PRV belongs to the family Herpesviridae, subfamily Alphaherpesvirinae, genus *Varicellovirus*.

This virus is used as a model of human herpes type 1.

The culture plates and the well inserts used come from the supplier Dutscher. The references of these plates and well inserts are the following:

Multiwell 6 well: ref: 3502.
Filter: ref: 3091.

2. Evaluation of the Leaktightness and of the Integrity of the Film Obtained With Composition A Prior to the evaluation of the impermeability of the film formed to the herpes virus, the leaktightness of the film with respect to the culture medium and its integrity during prolonged contact with said culture medium were demonstrated.

Composition A was introduced into one well of a 6-well plate. The amount added (0.5 to 1 cm) must be sufficient to be able to soak the well insert to a height of approximately 3 mm.

Using forceps, the well insert was soaked in the composition while holding it on a slant in order to avoid the formation of bubbles. Once the surface of the bottom of the well insert is completely in contact with the composition, the well insert was carefully removed.

The bottom of the well insert was scrapped with a spatula in order to remove the surplus product.

It was then placed upside down in order to dry the film.

The thickness of the film thus formed was about 30 μm.

8 "film-coated" well inserts were thus prepared.

a. Test for Leaktightness of the Film Obtained With Composition A:

Two "film-coated" well inserts and one film-free control well insert were introduced into the wells of a culture plate containing physiological saline (9 g/l NaCl).

The DMEM culture medium was introduced into each of the well inserts. The DMEM culture medium used for the present test is pink in color.

After 24 h at 37° C., it was observed that the physiological saline of the well containing the control well insert had become pink. The DMEM of the control well insert therefore migrated to the physiological saline medium.

The physiological saline of the well containing the "film-coated" well insert remained, for its part, colorless: the DMEM did not migrate.

These results show that the films formed with the compositions according to the present invention are culture medium-leaktight.

b. Test for Integrity of the film Obtained With Composition A:

The film obtained with composition A was brought into contact with the DMEM culture medium for 24 h at 37° C.

After 24 h, the film remains intact, and becomes just slightly opaque.

c. Test for the Barrier Effect of the Film According to the Invention With Respect to the Herpes Virus i. Method 3 ml of DMEM culture medium were introduced into 16 wells of 6-well plates.

Eight "film-coated" well inserts and eight non-film-coated well inserts (positive control) were placed in the wells.

200 μl of PRV viral suspension was added to each well insert.

The plates and well inserts were incubated at 37° C.±2° C. in the presence 5±0.5% $CO_2$.

After 1, 2, 4 and 6 hours of incubation, two "film-coated" well inserts and two non-film-coated well inserts per hour were removed from the plates in order to establish a time course.

Each supernatant is harvested individually in order to be titrated.

ii. Titration Protocol:

Each supernatant collected from the wells containing the "film-coated" well inserts was diluted to the nontoxic and nonvirucidal dilution of the product tested, i.e. to 1/10 and to 1/100 in dilution medium, and titrated on two 96-well plates as described hereinafter.

That is to say a total of thirty two 96-well plates.

Procedure

For each 96-well plate, 50 μl of dilution medium were added to each well. 25 μl of each diluted supernatant or of positive control were then added and homogenized in the eight wells of the first column of the first plate.

25 μl were then transferred from column 1 to column 2 (dilution to 1/3) and the solution was homogenized. This step was repeated from column 2 up to column 11.

25 μl were then transferred from column 11 (first plate) to column 1 (second plate). This step was repeated from column 2 up to column 11.

The columns 12 served as a cell control. 50 μl of a suspension of Vero cells at $2.5 \times 10^5$ cells/ml were added to all the wells.

The plates were then incubated for between 6 and 9 days at 37° C.±2° C. in the presence of 5%±0.5% of $CO_2$.

Titration Control

The PRV viral stock was titrated on one 96-well plate in parallel.

iii. Results

The results of the titrations of the positive controls and of the tests are given in table 1 below.

TABLE 1

| | Titration results | | | | |
|---|---|---|---|---|---|
| | Incubation time | Observation of the cytopathic effect (dilution to $10^{-1}$) | Titer as $TCID_{50}$/ml | Observation of the cytopathic effect (dilution to $10^{-2}$) | Titer as $TCID_{50}$/ml |
| Positive controls | 1 h | yes | $4.43\ 10^7$ (7.65) | | |
| | 2 h | yes | $1.74\ 10^7$ (7.24) | | |
| | 4 h | yes | $2.63\ 10^7$ (7.42) | | |
| | 6 h | yes | $1.7\ 10^8$ (8.23) | | |
| Film obtained with composition A | 1 h | no | $<3.26\ 10^3$ (<3.51) | no | $<3.26\ 10^4$ (<4.51) |
| | 2 h | no | $<3.26\ 10^3$ (<3.51) | no | $<3.26\ 10^4$ (<4.51) |
| | 4 h | no | $<3.26\ 10^3$ (<3.51) | no | $<3.26\ 10^4$ (<4.51) |
| | 6 h | no | $<3.26\ 10^3$ (<3.51) | no | $<3.26\ 10^4$ (<4.51) |

Contrary to the positive controls, no cytopathic effect was observed for the tests using a well insert "film-coated" with composition A according to the invention. These results therefore confirm the impermeability of the film formed by the composition according to the invention to PRV, a model of human herpes type 1, and the consistency of this impermeability throughout the application.

Example 3

Comparative test of the breaking strength of films formed from a composition according to the invention (composition A of example 1) and from comparative compositions not comprising boric acid (compositions B and C).

Composition B (without boric acid) comprised:

| Ingredient | % by weight |
|---|---|
| Ethylcellulose | 10 |
| Castor oil | 10 |
| Citric acid | 0.5 |
| Ethanol | 67.5 |
| Demineralized water | 12 |

The castor oil and the citric acid were added to the water/ethanol mixture with stirring maintained for 10 min. The ethylcellulose was then dispersed in the mixture. Composition B was recovered after stirring the mixture for 30 min.

A composition C (without boric and citric acid) was also prepared:

| Ingredient | % by weight |
| --- | --- |
| Ethylcellulose | 10 |
| Castor oil | 10 |
| Ethanol | 68 |
| Demineralized water | 12 |

The castor oil was added to the water/ethanol mixture with stirring maintained for 10 min. The ethylcellulose was then dispersed in the mixture. Composition C was recovered after stirring the mixture for 30 min.

Measurement of the Breaking Strength of the Films:

Compositions A, B and C were coated onto silicone polyester and dried in the open air. These coatings were carried out using a coating table which makes it possible to adjust the desired film thickness. In the present case, the film had a thickness of 50 µm.

A rectangular strip of film 15 mm wide and 150 mm long was cut out using a hole punch. This rectangular strip was then placed between the jaws of an MTS dynamometer (model DY30 with a 10-newton force sensor) which were 100 mm apart. A tensile test until breaking of the test specimen at a speed of 300 mm/min was then carried out.

The strain was calculated using the Testwork software, by taking the maximum point of the curve (break). The software thus gived the force required for breaking. The results have been reported in table 2 hereinafter.

TABLE 2

Results of the breaking strength measurements

| Characteristics | Composition A | Composition B | Composition C |
| --- | --- | --- | --- |
| Breaking force longitudinal direction (N/cm) | 1.6 | 1.4 | 1.2 |

The film-forming composition according to the invention requires a greater force than the others to become distorted, which confers on the film a better integrity throughout the application.

The invention claimed is:

1. A topical film-forming composition comprising, in a pharmaceutically acceptable medium:
    5% to 30% by weight of ethylcellulose;
    0.1% to 20% by weight of an auxiliary film-forming agent;
    0.1% to 5% by weight of one or more triacids, at least one of which is boric acid; and
    60% to 95% by weight of an organic solvent,
the percentages being expressed by weight, relative to the total weight of the composition.

2. The composition of claim 1, wherein the ethylcellulose is present in a content ranging from 8% to 20% by weight relative to the total weight of the composition.

3. The composition of claim 2, wherein the ethylcellulose is present in a content ranging from 8% to 15% by weight, relative to the total weight of the composition.

4. The composition of claim 1, wherein the auxiliary film-forming agent is chosen from oxyethylenated derivatives.

5. The composition of claim 4, wherein the oxyethylenated derivative is an oxyethylenated oil.

6. The composition of claim 5, wherein said oxyethylenated oil is vegetable oil.

7. The composition of claim 1, wherein the auxiliary film-forming agent is present in a content ranging from 2% to 12% by weight, relative to the total weight of the composition.

8. The composition as of claim 1, wherein the triacid comprises a mixture of boric acid and citric acid.

9. The composition of claim 8 wherein the mixture of boric acid and citric acid is in a weight ratio of between 1:2 and 2:1.

10. The composition of claim 1, wherein the organic solvent is chosen from alcohols which are liquid at ambient temperature.

11. The composition of claim 10, wherein the alcohol is selected from the group consisting of ethanol, isopropanol, diacetone alcohol, 2 butoxyethanol, cyclohexanol, and mixtures thereof.

12. The composition of claim 11, wherein the alcohol is ethanol.

13. The composition as of claim 1, wherein the organic solvent represents 65% to 85% by weight, relative to the total weight of the composition.

14. The composition of claim 1, wherein said composition further comprises water.

15. The composition of claim 14, wherein said water content is present ranging from 1% to 20% by weight of said composition.

16. The composition of claim 15 wherein said water content is present ranging from 5% to 15% by weight of said composition.

17. The composition of claim 1, wherein it does not contain any additional pharmaceutically active agent for the treatment of herpes.

18. A method for treating herpes, comprising the application of a composition as of claim 1.

19. A method according to claim 18 wherein treating herpes is herpes labialis.

* * * * *